US008658649B2

(12) United States Patent  
Gillespy et al.

(10) Patent No.: US 8,658,649 B2
(45) Date of Patent: Feb. 25, 2014

(54) KINASE INHIBITOR

(75) Inventors: Timothy A. Gillespy, Hillsborough, NJ (US); Paul Eynott, Bedminster, NJ (US); Elizabeth M. Allen, Stewartsville, NJ (US); Kin T. Yu, Chalfont, PA (US); Asher Zilberstein, Doylestown, PA (US)

(73) Assignee: Sanofi, Paris (FR)

( * ) Notice: Subject to any disclaimer, the term of this patent is extended or adjusted under 35 U.S.C. 154(b) by 911 days.

(21) Appl. No.: 12/401,254

(22) Filed: Mar. 10, 2009

(65) Prior Publication Data
US 2010/0035884 A1 Feb. 11, 2010

Related U.S. Application Data

(63) Continuation of application No. PCT/US2007/078103, filed on Sep. 11, 2007.

(60) Provisional application No. 60/825,168, filed on Sep. 11, 2006.

(51) Int. Cl.
A61K 31/4965 (2006.01)
A61K 31/50 (2006.01)
A61K 31/495 (2006.01)
A01N 43/58 (2006.01)
A01N 43/60 (2006.01)
C07D 413/00 (2006.01)
C07D 471/00 (2006.01)
C07D 487/00 (2006.01)
C07D 491/00 (2006.01)
C07D 495/00 (2006.01)
C07D 497/00 (2006.01)

(52) U.S. Cl.
USPC ....... 514/255.05; 514/249; 544/121; 544/350

(58) Field of Classification Search
USPC .................. 514/255.05, 249; 544/121, 350
See application file for complete search history.

(56) References Cited

U.S. PATENT DOCUMENTS

| 3,524,860 | A | 8/1970 | Albertson |
| 3,992,392 | A | 11/1976 | Gassman |
| 5,714,495 | A | 2/1998 | Viaud et al. |
| 6,770,643 | B2 | 8/2004 | Cox |
| 6,897,207 | B2 | 5/2005 | Cox et al. |
| 2001/0037031 | A1 | 11/2001 | Henkelmann et al. |
| 2002/0049205 | A1 | 4/2002 | Li et al. |
| 2003/0050320 | A1 | 3/2003 | Hashimoto et al. |
| 2003/0225036 | A1 | 12/2003 | Kolesnikov et al. |
| 2004/0009983 | A1* | 1/2004 | Cox et al. ............... 514/249 |
| 2004/0082635 | A1 | 4/2004 | Hashimoto et al. |
| 2011/0112101 | A1 | 5/2011 | Dharanipragada et al. |

FOREIGN PATENT DOCUMENTS

| AU | 200122094 B2 | 7/2001 |
| CA | 2 412 462 A1 | 12/2001 |
| EP | 0 509 974 A1 | 10/1992 |
| EP | 0 737 685 A1 | 10/1996 |
| EP | 1 086 950 A1 | 3/2001 |
| WO | WO 95/33748 A1 | 12/1995 |
| WO | WO 98/22457 A1 | 5/1998 |
| WO | WO 98/36035 A1 | 8/1998 |
| WO | WO 98/41525 A1 | 9/1998 |
| WO | WO 98/47899 A1 | 10/1998 |
| WO | WO 99/07703 A1 | 2/1999 |
| WO | WO 99/20624 A1 | 4/1999 |
| WO | WO 99/45016 A2 | 9/1999 |
| WO | WO 99/51233 A1 | 10/1999 |
| WO | WO 99/51596 A1 | 10/1999 |
| WO | WO 00/17202 A1 | 3/2000 |
| WO | WO 01/02369 A2 | 1/2001 |
| WO | WO 01/53268 A2 | 7/2001 |
| WO | WO 0147922 | 7/2001 |
| WO | WO 01/96336 A2 | 12/2001 |
| WO | WO 02/28831 A1 | 4/2002 |
| WO | WO 03000688 | 1/2003 |
| WO | WO 03000690 | 1/2003 |
| WO | WO 03/035065 A1 | 5/2003 |
| WO | WO 2004016614 | 2/2004 |
| WO | WO 2005014543 | 2/2005 |
| WO | WO 2006030031 | 3/2006 |
| WO | WO 2006042950 | 4/2006 |
| WO | WO 2006052712 | 5/2006 |

OTHER PUBLICATIONS

Vippagunta et al. Advanced Drug Delivery Reviews, 2001, vol. 48, pp. 3-26.*
U.S. Appl. No. 13/151,853, filed Jun. 2, 2011, Bordeau, et al.
U.S. Appl. No. 13/151,916, filed Jun. 2, 2011, Oligino, et al.
U.S. Appl. No. 13/257,476, filed Sep. 19, 2011, Lee, et al.
Yousefi, et al., Requirement of Lyn and Syk Tyrosine Kinases for the Prevention of Apoptosis by Cytokines in Human Eosinophils, J. Exp. Med., (1998), vol. 183, pp. 1407-1414.
Bischoff, et al., A homologue of Drosophila aurora kinase is oncogenic and amplified in human colorectal cancers, EMBO; 1998 (17) 11 pp. 3052-3065.
Bundgaard, et al., A Novel Solution-Stable, Water-Soluble Prodrug Type for Drugs Containing a Hydroxyl or an NH-Acidic Group, J. Med. Chem., 1989 (32) 12, pp. 2503-2507.

(Continued)

Primary Examiner — Samira Jean-Louis
(74) Attorney, Agent, or Firm — Scully, Scott, Murphy & Presser, P.C.

(57) ABSTRACT

The invention is directed to a compound of formula (I):

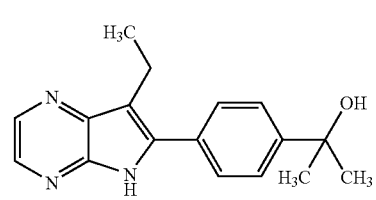

and the prodrugs, and pharmaceutically acceptable salts and solvates of such compounds and their prodrugs. Such a compound has valuable pharmaceutical properties, in particular the ability to inhibit protein kinases.

6 Claims, 10 Drawing Sheets

(56) References Cited

OTHER PUBLICATIONS

Chan, et. al., The Role of Protein Tyrosine Kinases and Protein Tyrosine Phosphatases in T Cell Antigen Receptor Signal Transduction, Annu. Rev. Immunol, 1994 (12) pp. 555-592.
Cheng, et al., Syk Tyrosine Kinase Required for Mouse Viability and B-Cell Development, Nature, vol. 378, (1995), pp. 303-306.
Chu, et al., The Syk Family of Protein Tyrosine Kinases in T-Cell Activation and Development, Immunological Reviews, vol. 165, pp. 167-180, (1998).
Costello, et al., Critical Role for the Tyrosine Kinase Syk in Signalling Through the High Affinity IgE. Receptor of Mast Cells, Oncogene, (1996), vol. 13, pp. 2595-2605.
Faris, et al., CD40 Signaling Pathway: Anti-CD40 Monoclonal Antibody Induces Rapid Dephosphorylation and Phosphorylation of Tyrosine-Phosphorylated Proteins Inducing Protein Tyrosine Kinase Lyn, Fyn, and Syk and the Appearance of a 28-kD Tyrosine Phosphorylated Protein, J. Exp. Med., vol. 179, (1994), pp. 1923-1931.
Folkman, J., et. al., Angiogenesis in cancer; vascular, rheumatoid and other disease, Nature Med.. 1995 (1) 1 pp. 27-31.
Hanks, et al., The Eukaryotic Protein Kinase Superfamily: Kinase (Catalytic) Domain Structure and Classification, FASEB. 1995 (9) pp. 576-596.
Hendricks-Taylor, et al., SLP-76 is a Substrate of the High Affinity IgE Receptor-Stimulated Protein Tyrosine Kinases in Rat Basophiiic Leukemia Cells, The Journal of Biological Chemistry, vol. 272, No. 2, (1997), pp. 1363-1367.
Ishial et al., BLNK Required for Coupling Syk to PLCy2 and Rac1-JNK in B Cells, Immunity: vol. 10, pp. 117-125, (1999).
Iwashita, et al., Signal Transduction System or Growth Factor Receptors Associated with Tyroslne Kinase Activity: Epidermal Growth Factor Receptor Signalling and its Regulation, Cellular Signalling, 1992 (4) 2 pp. 123-132.
Jekunen, A. P., et al., Inhibition of Malignant Angiogenesis, Cancer Treatment Reviews, vol. 23, pp. 263-286, (1997).
Newton, et.al., Protein Kinase C: Structure, Function, and Regulation, J. Biol. Chem, 1995 (270) 48 pp. 28495-28498.
Pines, Cyclins and cyclin-dependent kinases: take your partners, Trends in Biochemical Sciences. 1993 (18) pp. 195-197.
Reth, et al., Antigen Receptor Tail Clue, Nature, vol. 338, (1989), pp. 383-384.
Richardson et al., A mechanism for regulation of the adhesion-associated protein tyrosine kinase pp. 125 FAK, Nature, 1996 (380). pp. 538-540.
Sieg, et al., Required role of focal adhesion kinase (FAK) for integrin-stimulated cell migration, J. Cell Science, 1999 (112), pp. 2677-2691.
Van Oers, et al., The Syk/ZAP-70 Protein Tyrosine Kinase Connection to Antigen Receptor Signalling Processes, Siminars in Immunology, vol. 7, pp. 227-236, (1995).
Xu, et al., Attenuation of the Expression of the Focal Adhesion Kinase Induces Apoptosis in Tumor Ceils, Cell Growth & Differentiation, vol. 7, pp. 413-418, (1996).
Yanaga, et al., Syk Interacts With Tyrosine-Phosphorylated in Human Plateiets Activated by Collagen and Cross-Linking of the Fcy-IIA receptor. Biochem. J., (1995). pp. 471-478, vol. 311.
International Search Report for WO2008/033798 dated Mar. 20, 2008.
Boutin, J. A., et al., "Screening of ligand binding on melatonin receptor using non-peptide combinatorial libraries", Journal of Receptor and Signal Transduction Research 20(1):105-118 (2000).
Busev, A. I., et al., "Extraction-Photometric Determination of Molybdenum by Means of 6,7-Dihydroxy-2,4-Diphenylbenzopyrilium Chloride", Translated from Zhurnal Analiticheskol Khimii 16(5):578-584 (Sep.-Oct. 1961).
Caplus Chemical Abstract Service, US Database accession No. 1975 97992 XP002204303 & KHIM Geterotsiki Soedin No. 12 1974 1690-1694.
Caplus Chemical Abstract Service, US Database accession No. 1994-605262 XP002204304 & J Chem Tes S No. 7 1994 286-287.
Caplus Chemical Abstract Service, US Database accession No. 1995 505008 XP002204302, & J Indian Chem Soc vol. 70, 11-12, 1993, 1035-1042.
Casanova, B., et al., "A critical review of the current pathogenesis of multiple sclerosis and possible future trends", Rev Neurol. 28(9):909-15 (May 1, 1999).
Cecil Textbook of Medicine, 20th edition, vol. 2, 1992-1996 (1996), Edited by Bennett, J. C. et al.
Chumakov, Y., et al., "Preparation of vinylpyridines", Byul. Izobret. i Tovarnykh Znakov, 10: 22 (1964).
Clark, B. A., et al., Preparation of pyrrolo[2,3-b]pyrazines and pyrazino[2,3-b]indole, Chemical and Industry, 215-216 (Mar. 1, 1975).
Clark, B. A. J., et al., Formation of Certain Substitut d 5H-Pyrrolo[2,3-b]pyrazines by Thermal Cyclisation of Pyraxinylhydrazones and a Route to 5H-Pyrazino[2,3-b]in-dol; a Synthesis of 5H-Pyrrolo[2,3-b] pyraxine and Some of its Pr perties, p. 1361 (1976).
Clark, B. A. J., et al., "Mass Spectrometry of Pyrrolo[2,3-b]pyrazines and Pyraxino[2,3-b]indole", Organic Mass Spectrometry, 12(7):421-423 (1977).
Cooper, L. C., et al., "2-Aryl Indole NK1 Receptor Antagonists: Optimisation of Indole Substitution", Bioorganic & Medicinal Chemistry Letters, 11:1233-1236 (2001).
Database Crossfire Bellsterin Beilstein Institut zur Forderung der Chemischen Wissenschaften Frankfurt am main DE, XP002204305 & KHIM Fam. ZN, vol. 7 No. 6 1973, 18.
Davis, M. L., et al., "Reactions of β-(Lithiomethyl)azines with Nitriles as a Route to Pyrrolo-pyridines, —quinolines,— pyrazines,—quinoxalines and—pyrimidines", Tetrahedron, 48(5):939-952 (1992).
Essassi, E. M., et al., Sythese et heterocyclisation des Bulletin des SOC IhnS Chimiques Belges, vol. 96, 1, 1987, 63-67, XP008005414.
Finar, I. L., et al., "The Preparation and Some Reactions of 4-Formyl-1-phenyl-pyrazoles", 2733-2378 (1961).
Hands, D., et al., "A Convenient Method for the Preparation of 5-, 6- and 7-Azaindoles and Their Derivatives", Synthesis, 877-882 (Jul. 1996).
Hardy, C. R., et al., "Ring Opening or Rearrangement versus N-Oxidation in the Action of Peracids upon Pyrrolo[2,3- b]pyridines, Pyrrolo[2,3-b]pyrazines, and Triazolo[1,5-a]- and Triazolo 4,3-a-pyrazine. Some Chemical and Spectroscopic Properties of the Triazoloyprazines and Their N-Oxides", J.C.S. Perkin I, 506-511 (1980).
Henry, J. R., et al., "6-Amino-2-(4-fluorophenyl)-4-methoxy-3-(4-pyridyl)-1H-pyrrolo[2,3-b]pyridine (RWJ 68354): A Potent and Selective p38 Kinase Inhibitor", J. Med. Chem. 41:4196-4198 (1998).
Herbert, R., et al., "Synth ses and Pr perti s of 1H-Pyrrolo[2,3-b]pyridines", J. Chem. Soc. (C). 1505-1514 (1969).
Herbert, R., et al., "1H-Pyrrolo[2,3-b]pyridines. Part II. Fragmentation of Some 1H-Pyrrolo[2,3-b]pyridines induced by Electron Impact", J. Chem. Soc. (B), 459-463 (1970).
Hubert, A. J., et al., "Thermolyse von v-Triazolyl-Derivaten", Chem. Ber., 103:3811-3816 (1970).
Joshi, K.C., et al., "Investigation of the Reactions of 2-Hydrazino-benzimidazoles with β-diketones: Syntheses of 2-(3,5-Disubstituted-1H-pyrazol-1-yl)benzimidazoles", J. Heterocyclic Chem., 25:1641-1643, Nov.-Dec. 1988.
Liu, S., et al., Syntheses, Structures, and Electroluminescence of New Blue/Green Luminescent Chelate Compounds: Zn(2-py-in)2(Thf), BPh2(2-py-in), Be(2-py-in)2, and BPh2(2-py-aza) [2-py-in = 2-(2-pyridyl(indiol; 2-py-aza = 2-(2- pyridyl)-7-azaindole], J. Am. Chem. Soc. 122:3671-3678 (2000).
Mahabeleshwar, G. H., et al., "Syk, a Protein-tyrosine Kinase, Suppresses the Cell Motility and Nuclear Factor kB-mediated Secretion of Urokinase ype Plasminogen Activator by Inhibiting the Phosphatidylinositol 3'-Kinase Activity in Breast Cancer Cells", The Journal of Biological Chemistry, 278(8):6209-6221 (2003).

(56) References Cited

OTHER PUBLICATIONS

Marot, C., et al., "Pharmacophoric Search and 3D-QSAR Comparative Molecular Field Analysis Studies on Agonists of Melatonin Sheep Receptors" J. Med. Chem. 41(23):4453-4465 (1998).

Martin, C., et al., "Reactions Selectives De L'O.Chlorobenzonitrile : SNAr", Tetrahedron Letters, 30(6):935-936 (1989).

Nowakowski, J. et al., "Structures of the Cancer-Related Aurora-A, FAK, and EphA2 Protein Kinases from Nanovolume Crystallography"Structure, 10:1659-1667 (Dec. 2002).

Park, S. S., et al., "A Facile Synthesis of 2,3-Disubstituted Pyrrolol[2,3-b]pyridines via Palladium-Catalyzed Heteroannulation with Internal Alkynes", Tetrahedron Latters, 39:627-630 (1998).

Protiva, M., et al., Antihistamine substances. XXVI. Some new heterocyclic derivatives of ethylenediamine, Chemicke Listy pro Vedu a Prumyal, 46:551-554 (1952).

Rodriguez, A. L, et al., Angewandte Chemie International Edition 39(14): 2488-2490 (2000).

Ruggeri, B., et al., "CEP-7055: A Novel, Orally Active Pan Inhibitor of Vascular Endothelial Growth Factor Receptor Tyrosine Kinases with Potent Antiangiogenic Activity and Antitumor Efficacy in Preclinical Models", Cancer Research, 63:5978-5991 (Sep. 15, 2003) and Announcements (correction to article) 63:7542-7544 (Nov. 1, 2003).

Senga, K., et al., "Synthesis of Pyrazolo[1',5' : 1,2] 1,3,5-triazino[5,6-a]benzimidazoles", 12:899-901 (Oct. 1975).

Singh, S. P., et al., "Formation and dehydration of a series of 5-hydroxy-5-trifluoromethyl-4,5-dihydropyrazoles" Journal of Fluorine Chemistry, 94:199-203 (1999).

Soos, T., et al., "Novel Thermal Rearrangement of Fused Diaryl-v-Triazolium Salts to Neutral Indazole Derivatives. Fused Asolium Salts. 16", J. Org. Chem. 62:1136-1138 (1997).

Takagi, K., et al., "Synthesis of Pyrimidino[4,5-b][1,5]benzodiazepin-2-ones and Pyrimidino[1,6-a]benzimidazol-1-ones from 4-Ethoxycarbonylamino-1H-1,5-benzodiazpine-3-carbonitrile via 4-(2-Aminoanilino)pyrimidin-2(1H)-one-5-carbonitriles", J. Heterocyclic Chem., 23:1443-1449 (Sept-Oct 1986).

Vierfond, J., et al., "Cyclization par amination intramoleculaire dane la serie de la pyrazine", Tetrahedron Letters, 22 (17):1219-1222 (Nov. 25, 1980.

West, A. R., "Solid state chemistry and its applications, Chapter 10, Solid Solutions", pgs. 358 and 365, Mar. 3, 1988).

\* cited by examiner

\* P<0.05 \*\* P<0.001 compared to the vehicle group

***p<0.001 compared to the vehicle group

KINASE INHIBITOR

CROSS REFERENCE

Field of the Invention

This invention is directed to substituted azaindoles, their preparation, pharmaceutical compositions containing these compounds, and their pharmaceutical use in the treatment of disease states capable of being modulated by the inhibition of the protein kinases.

BACKGROUND OF THE INVENTION

Protein kinases participate in the signalling events which control the activation, growth and differentiation of cells in response to extracellular mediators and to changes in the environment. In general, these kinases fall into several groups; those which preferentially phosphorylate serine and/or threonine residues and those which preferentially phosphorylate tyrosine residues [S. K. Hanks and T. Hunter, FASEB. J., 1995, 9, pages 576-596]. The serine/threonine kinases include for example, protein kinase C isoforms [A. C. Newton, J. Biol. Chem., 1995, 270, pages 28495-28498] and a group of cyclin-dependent kinases such as cdc2 [J. Pines, Trends in Biochemical Sciences, 1995, 18, pages 195-197]. The tyrosine kinases include membrane-spanning growth factor receptors such as the epidermal growth factor receptor [S. Iwashita and M. Kobayashi, Cellular Signalling, 1992, 4, pages 123-132], and cytosolic non-receptor kinases such as p56tck, p59fYn, ZAP-70 and csk kinases [C. Chan et. al., Ann. Rev. Immunol., 1994, 12, pages 555-592].

Inappropriately high protein kinase activity has been implicated in many diseases resulting from abnormal cellular function. This might arise either directly or indirectly, for example by failure of the proper control mechanisms for the kinase, related for example to mutation, over-expression or inappropriate activation of the enzyme; or by over- or under-production of cytokines or growth factors also participating in the transduction of signals upstream or downstream of the kinase. In all of these instances, selective inhibition of the action of the kinase might be expected to have a beneficial effect.

Syk is a 72-kDa cytoplasmic protein tyrosine kinase that is expressed in a variety of hematopoietic cells and is an essential element in several cascades that couple antigen receptors to cellular responses. Thus, Syk plays a pivotal role in signalling of the high affinity IgE receptor, FcεR1, in mast cells and in receptor antigen signalling in T and B lymphocytes. The signal transduction pathways present in mast, T and B cells have common features. The ligand binding domain of the receptor lacks intrinsic tyrosine kinase activity. However, they interact with transducing subunits that contain immunoreceptor tyrosine based activation motifs (ITAMs) [M. Reth, Nature, 1989, 338, pages 383-384]. These motifs are present in both the β and γ subunits of the FcεR1, in the ξ-subunit the of T cell receptor (TCR) and in the IgGα and IgGβ subunits of the B cell receptor (BCR). [N. S. van Oers and A. Weiss, Seminars in Immunology, 1995, 7, pages 227-236] Upon binding of antigen and multimerization, the ITAM residues are phosphorylated by protein tyrosine kinases of the Src family. Syk belongs to a unique class of tyrosine kinases that have two tandem Src homology 2 (SH2) domains and a C terminal catalytic domain. These SH2 domains bind with high affinity to ITAMs and this SH2-mediated association of Syk with an activated receptor stimulates Syk kinase activity and localises Syk to the plasma membrane.

In Syk deficient mice, mast cell degranulation is inhibited, suggesting that this is an important target for the development of mast cell stabilising agents [P. S. Costello, Oncogene, 1996, 13, pages 2595-2605]. Similar studies have demonstrated a critical role for Syk in BCR and TCR signalling [A. M. Cheng, Nature, 1995, 378, pages 303-306, (1995) and D. H. Chu et al., Immunological Reviews, 1998, 165, pages 167-180]. Syk also appears to be involved in eosinophil survival in response to IL-5 and GM-CSF [S. Yousefi et al., J. Exp. Med., 1996, 183, pages 1407-1414]. Despite the key role of Syk in mast cell, BCR and T cell signalling, little is known about the mechanism by which Syk transmits downstream effectors. Two adaptor proteins, BLNK (B cell Linker protein, SLP-65) and SLP-76 have been shown to be substrates of Syk in B cells and mast cells respectively and have been postulated to interface Syk with downstream effectors [M. Ishiai et al., Immunity, 1999, 10, pages 117-125 and L. R. Hendricks-Taylor et al., J. Biol. Chem., 1997, 272, pages 1363-1367]. In addition Syk appears to play an important role in the CD40 signalling pathway, which plays an important role in B cell proliferation [M. Faris et al., J. Exp. Med., 1994, 179, pages 1923-1931].

Syk is further involved in the activation of platelets stimulated via the low-affinity IgG receptor (Fc gamma-RIIA) or stimulated by collagen [F. Yanaga et al., Biochem. J., 1995, 311, (Pt. 2) pages 471-478].

Focal adhesion kinase (FAK) is a non-receptor tyrosine kinase involved in integrin-mediated signal transduction pathways. FAK colocalizes with integrins in focal contact sites and FAK activation and its tyrosine phosphorylation have been shown in many cell types to be dependent on integrins binding to their extracellular ligands. Results from several studies support the hypothesis that FAK inhibitors could be useful in cancer treatment. For example, FAK-deficient cells migrate poorly in response to chemotactic signals and overexpression of C-terminal domain of FAK blocks cell spreading as well as chemotactic migration (Sieg et al, J. Cell Science, 1999, 112, 2677-2691; Richardson A. and Parsons T., Cell, 1997, 97, 221-231); in addition, tumor cells treated with FAK antisense oligonucleotides lost their attachment and underwent apoptosis (Xu et al, Cell Growth Differ. 1996, 4, 413-418). FAK has been reported to be overexpressed in prostate, breast, thyroid, colon and lung cancers. The level of expression of FAK is directly correlated with tumors demonstrating the most aggressive phenotype.

Angiogenesis or the formation of new blood vessels by sprouting from the preexisting vasculature is of central importance for embryonic development and organogenesis. Abnormal enhanced neovascularization is observed in rheumatoid arthritis, diabetic retinopathy and during tumor development (Folkman, Nat. Med., 1995, 1, 27-31.). Angiogenesis is a complex multistage process which includes activation, migration, proliferation and survival of endothelial cells. Extensive studies in the field of tumor angiogenesis in the past two decades have identified a number of therapeutic targets including kinases, proteases and integrins resulting in the discovery of many new anti-angiogenic agents, including KDR inhibitors some of which are currently under clinical evaluation (Jekunen, et al Cancer Treatment Rev. 1997, 23, 263-286.). Angiogenesis inhibitors may be used in frontline, adjuvant and even preventive settings for the emergence or regrowth of malignancies.

Several proteins involved in chromosome segregation and spindle assembly have been identified in yeast and *drosophila*. Disruption of these proteins results in chromosome missegregation and monopolar or disrupted spindles. Among these kinases are the Ipl1 and aurora kinases from *S. cerevi-* siae and drosophila respectively, which are required for centrosome separation and chromosome segregation. One human homologue of yeast Ipl1 was recently cloned and characterized by different laboratories. This kinase termed Aurora2, STK15 or BTAK belongs to the serine/threonine kinase family. Bischoff et al showed that Aurora2 is oncogenic and is amplified in human colorectal cancers (EMBO J, 1998, 17, 3052-3065). It has also been exemplified in cancers involving epithelial tumors such as breast cancer.

We have now found a novel substituted azaindole, which has valuable pharmaceutical properties, in particular, the ability to inhibit protein kinases, more particularly, the ability to selectively inhibit Syk kinase. This azaindole compound is related to those disclosed in U.S. Pat. No. 6,770,643 but is not specifically disclosed in that patent.

SUMMARY OF THE INVENTION

The present invention relates to a compound of formula I:

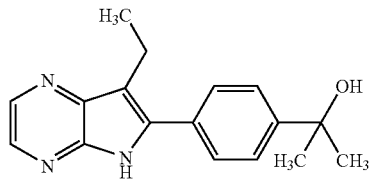

(I)

a pharmaceutically acceptable salt or prodrug thereof, or a solvate of such a compound, its salt or its prodrug.

The invention is also directed to a pharmaceutical composition comprising a compound of formula I, and method for using the compound of formula I for or treating or preventing a physiological condition related to Syk in a patient.

The invention is also directed to a process for preparing a compound that is an intermediate useful in preparing a compound of formula I.

In another aspect, the present invention is directed to pharmaceutical compositions comprising compounds of general formula (I):

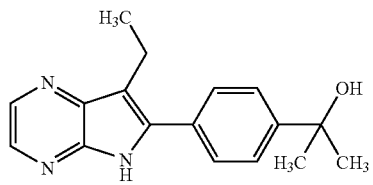

(I)

the corresponding N-oxide, and the prodrug; and a pharmaceutically acceptable salt and solvate (e.g. hydrate) of such a compound; and the N-oxide and the prodrug; together with one or more pharmaceutically acceptable carrier or excipient.

DETAILED DESCRIPTION OF THE INVENTION

Figure 1:
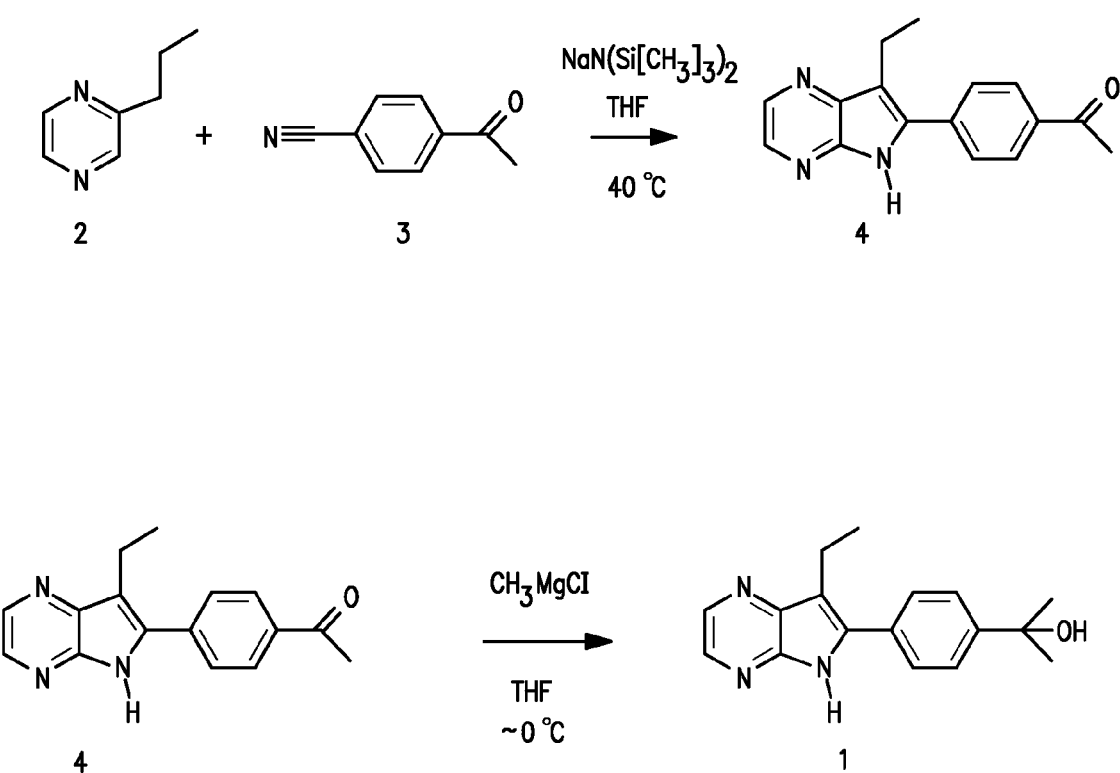
FIG. 1: Reaction scheme for making a compound of Formula I.

Thus, in one aspect, the present invention is directed to pharmaceutical compositions comprising a compound of general formula (I):

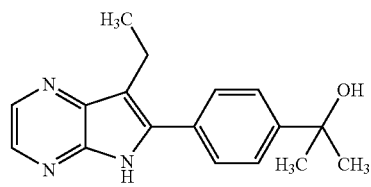

(I)

which also may be known as: 2-[4-(7-Ethyl-5H-pyrrolo[2,3-b]pyrazin-6-yl)-phenyl]-propan-2-ol.

In the present specification, the term "compound of the invention", and equivalent expressions, are meant to embrace a compound of general formula (I) as hereinbefore described, which expression includes the prodrugs, the pharmaceutically acceptable salts, and the solvates, e.g. hydrates, where the context so permits. Similarly, reference to intermediates, whether or not they themselves are claimed, is meant to embrace their salts, and solvates, where the context so permits. For the sake of clarity, particular instances when the context so permits are sometimes indicated in the text, but these instances are purely illustrative and it is not intended to exclude other instances when the context so permits.

Abbreviations used herein:
ATP adenosine triphosphate
DTT dithiothreitol
PBS phosphate buffered saline As used above, and throughout the description of the invention, the following terms, unless otherwise indicated, shall be understood to have the following meanings:

"Patient" includes both human and other mammals.

"Prodrug" means a compound which is convertible in vivo by metabolic means (e.g. by hydrolysis) to a compound of formula (I), including N-oxides thereof. For example an ester of a compound of formula (I) containing a hydroxy group may be convertible by hydrolysis in vivo to the parent molecule. Alternatively, an ester of a compound of formula (I) containing a carboxy group may be convertible by hydrolysis in vivo to the parent molecule.

Suitable esters of compounds of formula (I) containing a hydroxy group are, for example acetates, citrates, lactates, tartrates, malonates, oxalates, salicylates, propionates, succinates, fumarates, maleates, methylene-bis-β-hydroxynaphthoates, gentisates, isethionates, di-p-toluoyltartrates, methanesulfonates, ethanesulfonates, benzenesulfonates, p-toluenesulfonates, cyclohexylsulfamates and quinates.

An especially useful class of esters of compounds of formula (I) containing a hydroxy group, may be formed from acid moieties selected from those described by Bundgaard et. al., J. Med. Chem., 1989, 32, page 2503-2507, and include substituted (aminomethyl)-benzoates, for example dialkylamino-methylbenzoates in which the two alkyl groups may be joined together and/or interrupted by an oxygen atom or by an optionally substituted nitrogen atom, e.g. an alkylated nitrogen atom, more especially (morpholino-methyl)benzoates, e.g. 3- or 4-(morpholinomethyl)-benzoates, and (4-alkylpiperazin-1-yl)benzoates, e.g. 3- or 4-(4-alkylpiperazin-1-yl)benzoates.

Some of the compounds of the present invention are basic, and such compounds are useful in the form of the free base or in the form of a pharmaceutically acceptable acid addition salt thereof.

Acid addition salts are a more convenient form for use; and in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the patient in pharmaceutical doses of the salts, so that the beneficial inhibitory effects inherent in the free base are not vitiated by side effects ascribable to the anions. Although pharmaceutically acceptable salts of said basic compounds are preferred, all acid addition salts are useful as sources of the free base form even if the particular salt, per se, is desired only as an intermediate product as, for example, when the salt is formed only for purposes of purification, and identification, or when it is used as intermediate in preparing a pharmaceutically acceptable salt by ion exchange procedures. Pharmaceutically acceptable salts within the scope of the invention include those derived from mineral acids and organic acids, and include hydrohalides, e.g. hydrochlorides and hydrobromides, sulfates, phosphates, nitrates, sulfamates, acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methane-sulfonates, ethanesulfonates, benzenesulfonates, p-toluenesulfonates, cyclohexylsulfamates and quinates.

As well as being useful in themselves as active compounds, salts of compounds of the invention are useful for the purposes of purification of the compounds, for example by exploitation of the solubility differences between the salts and the parent compounds, side products and/or starting materials by techniques well known to those skilled in the art.

The compounds of the invention exhibit useful pharmacological activity and accordingly are incorporated into pharmaceutical compositions and used in the treatment of patients suffering from certain medical disorders. The present invention thus provides, according to a further aspect, compounds of the invention and compositions containing compounds of the invention for use in therapy.

Compounds within the scope of the present invention inhibit or block kinase catalytic activity according to tests described in the literature and described in vitro procedures hereinafter, and which tests results are believed to correlate to pharmacological activity in humans and other mammals. Thus, in a further embodiment, the present invention provides compounds of the invention and compositions containing compounds of the invention for use in the treatment of a patient suffering from, or subject to, conditions which can be ameliorated by the administration of protein kinase inhibitors (e.g. Syk, FAK, KDR or Aurora2). For example, compounds of the present invention are useful in the treatment of inflammatory diseases, for example asthma: inflammatory dermatoses (e.g. psoriasis, dematitis herpetiformis, eczema, necrotizing and cutaneous vasculitis, bullous disease); allergic rhinitis and allergic conjunctivitis; joint inflammation, including arthritis, rheumatoid arthritis and other arthritic conditions such as rheumatoid spondylitis, gouty arthritis, traumatic arthritis, rubella arthritis, psoriatic arthritis and osteoarthritis. The compounds are also useful in the treatment of Chronic Obstructive Pulmonary Disease (COPD), acute synovitis, autoimmune diabetes, autoimmune encephalomyelitis, collitis, atherosclerosis, peripheral vascular disease, cardiovascular disease, multiple sclerosis, restenosis, myocarditis, B cell lymphomas, systemic lupus erythematosus, graft versus host disease and other transplant associated rejection events, cancers and tumors (such as colorectal, prostate, breast, thyroid, colon and lung cancers) and inflammatory bowel disease. Additionally, the compounds are useful as tumor anti-angiogenic agents. And furthermore, the compounds of the invention are useful as agents to control tumor cells.

A special embodiment of the therapeutic methods of the present invention is the treating of joint inflammation.

Another special embodiment of the therapeutic methods of the present invention is the treating of rheumatoid arthritis.

A special embodiment of the therapeutic methods of the present invention is the treating of cancers, tumors and other proliferative disorders.

Another special embodiment of the therapeutic methods of the present invention is the treating of cancers involving liquid tumors.

Another special embodiment of the therapeutic methods of the present invention is the treating of mantle cell lymphoma.

Yet another special embodiment of the therapeutic methods of the present invention is the treating of disorders by inhibition of angiogenesis.

According to a further feature of the invention there is provided a method for the treatment of a human or animal patient suffering from, or subject to, conditions which can be ameliorated by the administration of a protein kinase inhibitor (e.g. Syk, FAK, KDR or Aurora2) for example conditions as hereinbefore described, which comprises the administration to the patient of an effective amount of a compound of the invention or a composition containing a compound of the invention. "Effective amount" is meant to describe an amount of compound of the present invention effective in inhibiting the catalytic activity a protein kinase, such as Syk, FAK, KDR or Aurora2, and thus producing the desired therapeutic effect.

References herein to treatment should be understood to include prophylactic therapy as well as treatment of established conditions.

The present invention also includes within its scope pharmaceutical compositions comprising a compound of the invention in association with a pharmaceutically acceptable carrier or excipient.

A compound of the invention may be administered by any suitable means. In practice a compound of the present invention may generally be administered parenterally, topically, rectally, orally or by inhalation; especially by the oral route or by inhalation.

Compositions according to the invention may be prepared according to the customary methods, using one or more pharmaceutically acceptable adjuvants or excipients. The adjuvants comprise, inter alia, diluents, sterile aqueous media and the various non-toxic organic solvents. The compositions may be presented in the form of tablets, pills, granules, powders, aqueous solutions or suspensions, injectable solutions, elixirs or syrups, and can contain one or more agents chosen from the group comprising sweeteners, flavourings, colourings, or stabilisers in order to obtain pharmaceutically acceptable preparations. The choice of vehicle and the content of active substance in the vehicle are generally determined in accordance with the solubility and chemical properties of the active compound, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulfate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

For parenteral administration, emulsions, suspensions or solutions of the products according to the invention in vegetable oil, for example sesame oil, groundnut oil or olive oil, or aqueous-organic solutions such as water and propylene glycol, injectable organic esters such as ethyl oleate, as well as sterile aqueous solutions of the pharmaceutically acceptable salts, are used. The solutions of the salts of the products according to the invention are especially useful for administration by intramuscular or subcutaneous injection. The aqueous solutions, also comprising solutions of the salts in pure distilled water, may be used for intravenous administration with the proviso that their pH is suitably adjusted, that they are judiciously buffered and rendered isotonic with a sufficient quantity of glucose or sodium chloride and that they are sterilised by heating, irradiation or microfiltration.

For topical administration, gels (water or alcohol based), creams or ointments containing compounds of the invention may be used. Compounds of the invention may also be incorporated in a gel or matrix base for application in a patch, which would allow a controlled release of compound through the transdermal barrier.

For administration by inhalation compounds of the invention may be dissolved or suspended in a suitable carrier for use in a nebuliser or a suspension or solution aerosol, or may be absorbed or adsorbed onto a suitable solid carrier for use in a dry powder inhaler.

Solid compositions for rectal administration include suppositories formulated in accordance with known methods and containing at least one compound of the invention.

The percentage of active ingredient in the compositions of the invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally from about 0.001 to about 50, preferably about 0.001 to about 5, mg/kg body weight per day by inhalation, from about 0.01 to about 100, preferably 0.1 to 70, more especially 0.5 to 10, mg/kg body weight per day by oral administration, and from about 0.001 to about 10, preferably 0.01 to 1, mg/kg body weight per day by intravenous administration. In each particular case, the doses will be determined in accordance with the factors distinctive to the subject to be treated, such as age, weight, general state of health and other characteristics which can influence the efficacy of the medicinal product.

The compounds according to the invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. Of course, for some patients, it will be necessary to prescribe not more than one or two doses per day.

Compounds of the invention may be prepared by the application or adaptation of known methods, by which is meant methods used heretofore or described in the literature, for example those described by R. C. Larock in Comprehensive Organic Transformations, VCH publishers, 1989.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in "Protective Groups in Organic Chemistry" John Wiley and Sons, 1991.

It will be appreciated that compounds of the present invention may contain asymmetric centres. These asymmetric centres may independently be in either the R or S configuration. It will be apparent to those skilled in the art that certain compounds of the invention may also exhibit geometrical isomerism. It is to be understood that the present invention includes individual geometrical isomers and stereoisomers and mixtures thereof, including racemic mixtures, of compounds of formula (I) hereinabove. Such isomers can be separated from their mixtures, by the application or adaptation of known methods, for example chromatographic techniques and recrystallisation techniques, or they are separately prepared from the appropriate isomers of their intermediates.

According to a further feature of the invention, acid addition salts of the compounds of this invention may be prepared by reaction of the free base with the appropriate acid, by the application or adaptation of known methods. For example, the acid addition salts of the compounds of this invention may be prepared either by dissolving the free base in water or aqueous alcohol solution or other suitable solvents containing the appropriate acid and isolating the salt by evaporating the solution, or by reacting the free base and acid in an organic solvent, in which case the salt separates directly or can be obtained by concentration of the solution.

The acid addition salts of the compounds of this invention can be regenerated from the salts by the application or adaptation of known methods. For example, parent compounds of the invention can be regenerated from their acid addition salts by treatment with an alkali, e.g. aqueous sodium bicarbonate solution or aqueous ammonia solution.

Compounds of this invention can be regenerated from their base addition salts by the application or adaptation of known methods. For example, parent compounds of the invention can be regenerated from their base addition salts by treatment with an acid, e.g. hydrochloric acid.

Compounds of the present invention may be conveniently prepared, or formed during the process of the invention, as solvates (e.g. hydrates). Hydrates of compounds of the present invention may be conveniently prepared by recrystallisation from an aqueous/organic solvent mixture, using organic solvents such as dioxan, tetrahydrofuran or methanol.

According to a further feature of the invention, base addition salts of the compounds of this invention may be prepared by reaction of the free acid with the appropriate base, by the application or adaptation of known methods. For example, the base addition salts of the compounds of this invention may be prepared either by dissolving the free acid in water or aqueous alcohol solution or other suitable solvents containing the appropriate base and isolating the salt by evaporating the solution, or by reacting the free acid and base in an organic solvent, in which case the salt separates directly or can be obtained by concentration of the solution.

The starting materials and intermediates may be prepared by the application or adaptation of known methods, for example methods as described in the Example or their obvious chemical equivalents.

The present invention is further Exemplified but not limited by the following illustrative Example.

300 MHz $^1$H nuclear magnetic resonance spectra (NMR) were recorded on a Varian Mercury instruments. In the nuclear magnetic resonance spectra (NMR) the chemical shifts (δ) are expressed in ppm relative to tetramethylsilane. Abbreviations have the following significances: s=singlet; d=doublet; t=triplet; m=multiplet; q=quartet; dd=doublet of doublets; ddd=doublet of double doublets.

High Pressure Liquid Chromatography-Mass Spectrometry (LCMS) experiments to determine retention times ($R_T$) and associated mass ions are performed using the following method. Mass Spectra (MS) are recorded using a Micromass LCT time of flight mass spectrometer. The method is positive electrospray ionization, scanning mass m/z from 100 to 1000. Liquid chromatography is performed on an Agilent™ 1100 Series Binary Pump & Degasser; stationary phase: Phenomenex Synergi™ 2μ Hydro-RP 20×4.0 mm column, mobile phase: A=0.1% formic acid (FA) in water, B=0.1% FA in acetonitrile. Injection volume of 5 μL by CTC Analytical PAL System. Flow is 1 mL/minute. Gradient is 5% B to 90% B in 3 minutes and 90% B to 100% B in 2 minutes. Auxiliary detectors are: Agilent 1100 Series UV detector, wavelength=220 nm and Sedere SEDEX™ 75 Evaporative Light Scattering (ELS) detector temperature=46° C., Nitrogen pressure=4 bar.

The thin layer chromatography (TLC) $R_F$ values were determined using Merck™ silica plates.

EXAMPLE 1

2-[4-(7-Ethyl-5H-pyrrolo[2,3-b]pyrazin-6-yl)-phenyl]-propan-2-ol

A total of 6.0 g of 2-[4-(7-ethyl-5H-pyrrolo[2,3-b]pyrazin-6-yl)phenyl]propan-2-ol (compound 1) was prepared in two steps from n-propylpyrazine (compound 2) and 4-acetylbenzonitrile (compound 3).

The synthesis of compound 1 was carried out as follows. Coupling of n-propylpyrazine (compound 2) and 4-acetylbenzonitrile (compound 3) with sodium bis(trimethylsilyl)amide in tetrahydrofuran at 40° C. gave the intermediate compound 4 in 30% yield. Reaction of compound 4 with methylmagnesium chloride in tetrahydrofuran at 0° C. gave the desired compound 1 in 74% yield after recrystallization from 2-propanol. The synthesis is shown in FIG. 1.

EXPERIMENTAL

2-[4-(7-Ethyl-5H-pyrrolo[2,3-b]pyrazin-6-yl)phenyl] ethanone (compound 4). A solution of n-propylpyrazine (compound 2, 912 mg, 7.46 mmol) in tetrahydrofuran (5 mL) was added drop-wise, over a period of seven minutes, to a solution of sodium bis(trimethylsilyl)amide (2M solution in THF; 13 mL, 26 mmol, 3.5 equiv) at 20° C. A deep, purple-red solution was obtained and the temperature fell to 16.4° C. A solution of 4-acetylbenzonitrile (compound 3, 1.08 g, 7.4 mmol) in tetrahydrofuran (5 mL) was added, over a period of 18 minutes, at 13.3° C. The temperature fell to 12.6° C. and a brown solution ensued. The mixture was stirred at room temperature for one hour, heated to about 35° C. for six hours, then left to stir at room temperature for about 60 hours. The mixture was poured into aqueous saturated sodium bicarbonate (200 mL) and extracted with ethyl acetate (2×150 mL). The ethyl acetate was washed with water (100 mL) and concentrated on the Buchi at a bath temperature of 40° C. and from 80 to 10 torr to give a deep-yellow solid. The solid was triturated with diethyl ether (25 mL), filtered and washed with ether (25 mL). The solid was air dried to give 600 mg (30.3%) of compound 4 as a yellow solid: $^1$H NMR (300 MHz, CDCl$_3$, FIG. 1) δ 8.5 (1H, d, J=2 Hz), 8.15 (2H, d, J=8 Hz), 8.1 (1H, d, J=3 Hz), 7.9 (2H, d, J=8 Hz), 3.1 (2H, q, J=9 Hz), 2.7 (3H, s), 1.4 (3H, t, J=9 Hz).

1-[4-(7-Ethyl-5H-pyrrolo[2,3-b]pyrazin-6-yl)phenyl]propan-2-ol (compound 1). To a cooled (~5° C.) solution of methylmagnesium chloride (3M in THF; 81.3 mL, 244 mmol, 10 equiv.) in tetrahydrofuran (116 mL), was added a solution of compound 4 (6.5 g, 24.4 mmol) in tetrahydrofuran (348 mL) drop-wise, over ninety minutes, keeping the temperature at about 0° C. by the rate of addition. A bright yellow solution was observed on addition. After one hour, TLC (ethyl acetate/n-heptane 1/1) showed no starting material present and a new spot moving at a lower $R_f$. The batch was quenched by the careful addition of a saturated, aqueous solution of sodium bicarbonate (about 660 mL). A thick mass ensued and ethyl acetate (250 mL) and water (250 mL) were added to the mixture. The aqueous layer was removed and re-extracted with ethyl acetate (2×250 mL). The ethyl acetate fractions were combined, washed with water (2×200 mL) and concentrated on the Buchi at a bath temperature of 40° C. and from 80 to 10 torr, to give 7.5 g (109%) of 1 as a light-beige solid: $^1$H NMR (DMSO-d$_6$, FIG. 2) δ 12.0 (1H, s), 8.35 (1H, d, J=3.5 Hz), 8.2 (1H, d, J=3.5 Hz), 7.6 (4H, s), 5.1 (1H, s), 2.9 (2H, q, J=8 Hz), 1.5 (6H, s), 1.3 (3H, t, J=8 Hz).

This material was combined with material from a previous experiment. The combined material (8.5 g) was refluxed with 2-propanol (150 mL) to give a clear, light brown solution, which was filtered hot through a hot Buchner funnel, under vacuum. A precipitate formed in the filter flask and the mixture was heated to boiling to give a clear solution. The material was allowed to cool to room temperature with stirring, to give a light, yellow solid, which was filtered, washed with cold 2-propanol and dried in the vacuum oven at 50° C. to give 6.0 g (71%) of compound 1 as a light, yellow solid: LCMS: R$_T$=2.55 minutes, MS: 282 (M+H); $^1$H NMR (DMSO-d$_6$, FIG. 3) δ 12.0 (1H, s), 8.35 (1H, d, J=3 Hz), 8.2 (1H, d, J=3 Hz), 7.6 (4H, s), 5.1 (1H, s), 2.9 (2H, q, J=9 Hz), 1.5 (6H, s), 1.3 (3H, t, J=9 Hz).

The elemental analysis of the compound 1 is shown in TABLE 1.

TABLE 1

| THEORY PERCENT PER ELEMENT: | C 72.57%, H 6.81%, N 14.93%, O 5.69% |
|---|---|
| EXPERIMENTAL 1: | C 72.46%, H 7.05%, N 15.07% |

In Vitro Test Procedure for Syk

Assay Name: Spleen Tyrosine (Y) Kinase
Short Name: Syk
Assay Format: Substrate Phosphorylation
Detection Format: Streptavidin FlashPlate
Modulation: Inhibition Streptavidin FlashPlate Plus microplates from PerkinElmer Life Sciences™ are designed for in-plate radiometric assays. The interior of each well is permanently coated with a thin layer of polystyrene-based scintillant followed by covalent binding of Streptavidin. These plates are suitable for a wide variety of assay applications which utilize biotinylated capture molecules. Poly (Glu,Tyr) 4:1 (PGT) is a random copolymer that can act as a substrate for tyrosine-specific protein kinases. The assay measures the phosphorylation of PGT-Biotin substrate by Syk. The enzyme transfers the [γ$^{33}$P]-phosphate from [γ$^{33}$P]-ATP to the polymeric substrate. The assay was run in solution in a non-binding 384-well plate. After stopping the reaction using phosphoric acid, the reaction mixture was transferred to a 384-well Streptavidin Flashplate. The biotinylated substrate was captured onto the plate and other reagents including hot ATP were washed away. Each well was then counted for radioactivity.

The enzyme reaction was run in a 384-well non-binding plate. Final reagent concentration/well was: 7.77 nM Syk, 15.5 nM PGT-Biotin substrate, 0.1 μCi $^{33}$P-ATP, 50 mM Tris, pH 7.5, 10 mM MgCl$_2$, 3 mM MnCl$_2$, 1 mM DTT, 0.1 mg/ml γ-Globulins. The reaction volume was: 22 μl. Reaction time: 120 minutes. Temperature: Room temperature. The reaction was stopped by addition of 20 μl of 9% Phosphoric acid and 30 μl of reaction mixture was transferred to a 384-well Streptavidin Flashplate. After 90 minutes of incubation at room temperature, the plate was washed with 0.02% of Tween-20 in 50 mM Tris, pH 7.5. Radioactivity was counted on a Top Count™ scintillation counter.

Enzyme dilution was prepared and kept on ice prior to use. MnCl$_2$ and DTT was added fresh into the assay buffer prior to use.

Materials for the assay are shown in Table 2.

TABLE 2

| Materials | Supplier | Catalog Number | Mwt | Function |
|---|---|---|---|---|
| 1 M Tris, pH 7.5 | Fisher | BP1757-500 | | Buffer |
| 1 M MgCl$_2$ | Sigma | M-1028 | 95.2 | Enzyme cofactor |
| 1 MnCl$_2$ | Sigma | M-1787 | 125.8 | Enzyme cofactor |
| DTT | Sigma | D-5545 | 154.2 | Antioxidant |
| γ-Globulins | Sigma | G-5009 | | Protein stabilizer |
| DMSO | Sigma-Aldrich | 15,493-9 | | Solvent |
| Staurosporine | Sigma | S-4400 | 466.5 | Reference inhibitor |
| Phosphoric acid (85%) | Sigma | P-6560 | 98.0 | Stop solution |
| 1 mCi [γ33P]-ATP | PerkinElmer | NEG6xx | | Substrate |
| 10 x PBS, pH 7.4 | Fisher | BP399-1 | | Wash buffer |
| Tween 20 | Fisher | BP337-500 | 1227.54 | Detergent |
| 384-well polypropylene plate | Corning | 3657 | | Compound plate |
| Non-binding 384-well plate | Corning | 3652 | | Reaction plate |
| 384-well Streptavidin Flashplate | PerkinElmer | SMP-410 (A) | | Capture plate |
| Top Seal A sealing film | Packard | 6005185 | | Plate sealer |
| Elx405 Automated Washer | Bio-Tek | | | Plate washer |
| Top Count | Packard | | | Counter |
| FX Station | Beckman | | | Liquid handler |
| Beckman 2000 | Beckman | | | Liquid handler |

Enzyme:
Flag-tagged Syk (0.184 mg/ml, MW=35,531.81 Da) was produced and purified by methods known in the art.

Substrate:
Biotin conjugated Poly (Glu,Tyr) 4:1 was purchased from Cisbio International™ (catalog #61 GT0BLB, lot #16).

Assay solutions used are shown in Table 3.

TABLE 3

| Reagent | Chemicals | Solvent | Concentration |
|---|---|---|---|
| Assay Buffer | Tris, pH 7.5 | H$_2$O | 50 mM |
| MnCl$_2$ and DTT add fresh | MnCl$_2$ | | 3 mM |
| | MgCl$_2$ | | 10 mM |
| | DTT | | 1 mM |
| | γ-globulins | | 0.1% |
| Enzyme & Substrate Solution | Syk | Assay buffer | 7.77 nM |
| Keep in non-binding plates | PGT-Biotin substrate | | 15.5 nM |
| ATP/$^{33}$P-ATP Solution | ATP/$^{33}$P-ATP | Assay buffer | 0.1 μCi/well |
| Stop Solution | Phosphoric acid | H$_2$O | 9% |
| Wash Buffer | Tween-20 | 1 x PBS, pH 7.4 | 0.02% |

Compound Dilution:
1. Compounds were received as 10 μl/well of 10 mM in 100% DMSO in a 96-well U-bottom polypropylene plate with Row H empty. Added 90 μl/well of 100% DMSO to yield 100 μl of 1 mM compound, resealed and stored the plate at room temperature in the dark.

2. Prepared compound destination plate: In a 384-well round-bottom polypropylene plate (Corning storage plate), added 23 µl/well of H$_2$O to columns 3 & 13, 20 µl/well of 30% DMSO to columns 4 through 12 and columns 14 through 22 (leaving Rows O and P empty).
3. Prepared compound dilutions (10 dilutions, 300 µM, 100 µM, 30 µM, - - - etc) on Biomek 2000™ using Kinase Profiling program: Using 20 µl tips with 8$^{th}$ one (Row H) removed, transferred 10 µl/well of 1 mM compound from Column 1 in source plate to Column 3 in destination plate to make the first 300 µM dilution. After that, in destination plate, mixed and transferred 10 ul/well of 300 µM dilution from column 3 to 4 to make the 100 µM dilution. Mixed and transferred 10 ul/well of 100 µM dilution from column 4 to 5 to make the 30 µM dilution, - - - etc. Made duplicate dilutions for each compound, for example, transferred 10 µl/well of compound from A1 in source plate to A3 and B3 in destination plate. Repeated mixing and transferred. Then, transferred 10 µl/well of 1 mM compound from Column 2 in source plate to Column 13 in destination plate to make the 300 µM dilution. After that, in destination plate, mixed and transferred 10 ul/well of 300 µM dilution from column 13 to 14 to make the 100 µM dilution - - - etc. One full 96-well source plate with Row H empty can make up to six compound destination plates.
4. Prepared standard compound parent plate: Added 5 µl/well of 10 mM Roscovitine solution in 100% DMSO to H1 and H2 in a 96-well U-bottom polypropylene plate, then diluted to 1 mM solution with 45 µl/well of 100% DMSO.
5. Preparee standard compound destination plate: In a 384-well round-bottom polypropylene plate (Corning™ storage plate), added 23 µl/well of H$_2$O to columns 3 & 13, 20 µl/well of 30% DMSO to columns 4 through 12 and columns 14 through 22 (Rows O and P only).
6. Prepared standard compound dilutions (10 dilutions, 300 µM, 100 u µM, 30 u µM, - - - etc) on Biomek 2000™ using Profiling Standard program: Using single 20 µl tip transferred 10 µl/well of 1 mM standard compound from H1 in parent plate to O1 in destination plate to make the first 300 µM dilution. After that, in destination plate, mixed and transferred 10 ul/well of 300 µM dilution from O3 to O4 to make the 100 µM dilution. Mixed and transferred 10 ul/well of 100 µM dilution from O4 to O5 to make the 30 µM dilution, - - - etc. Made duplicate dilutions for each standard compound, for example, transferred 10 µl/well of compound from H1 in parent plate to O3 and P3 in destination plate. Repeated mixing and transferred. Then, transferred 10 µl/well of 1 mM compound from H2 in parent plate to O13 in destination plate to make the 300 µM dilution. After that, in destination plate, mixed and transferred 10 ul/well of 300 µM dilution from O13 to O14 to make the 100 µM dilution - - - etc.
7. In standard compound destination plate, added 20 µl/well of 30% DMSO (high control) to A through H and 20 µl/well of 45% H$_3$PO$_4$ (low control) to I through J in column 23.

Assay Procedure:
1. To the assay plate (Corning™ Non-binding 384-well plate), added 10 µl Enzyme & Substrate Solution, 2 µl of test compound, incubate at room temperature for 30 min (enzyme/compound pre-incubation step).
2. Started Reaction by adding 10 µl ATP/$^{33}$P-ATP Solution.
3. Incubated at room temperature for 120 min.
4. Stopped the reaction by adding 20 µl Stop Buffer.
5. Transferred 30 µl of reaction mixture to a 384-well Streptavidin Flashplate.
8. Incubated at room temperature for 90 min.
9. Washed Streptavidin Flashplate 2 times with 100 µl/well of Wash Buffer using Elx405 Automated Washer.
10. Sealed and read the plate (40 sec/well) on Top Count™ scintillation counter.
*Ran assay from step 1 to step 5 using Biomek™ FX station.

Equation for curve fitting in IC$_{50}$ determination:

$$Y = \text{Bottom} + (\text{Top} - \text{Bottom})/(1 + 10^{((\text{LogIC}_{50} - X) * \text{Hill-Slope})})$$

X is the logarithm of concentration.
Y is the response.
Y starts at Bottom and goes to Top with a sigmoid shape.
This is identical to the "four parameter logistic" equation.
The compound of Formula I resulted in an IC$_{50}$ of 1.7 nanoMolar with this assay.

Viability Assay of Hematological Malignant Cell Lines Using MTS Reagent

1. Purpose
This method is to determine the viability of a liquid tumor cell line following treatment with a test compound. Tumor cells are maintained in suspension at log phase growth. On the day of use, cells are resuspended to a density of 0.05 to 0.1 million/ml and cells are incubated in 96 well plate with the test compounds for 96 hours. Viability of cells was measured by incubating cells with Promega's MTS reagent. The viability of the cell is proportional to the change in absorbance at 490 nm. By comparing the absorbance between control and compound-treated cells, the impact of the test compounds on the cell viability is determined as a percent of the control cell viability.

2. Procedure
    A. Materials
1. Cells:
    Liquid tumor cell lines are obtained from either American Tissue Culture Collection or from DSMZ (Deutsche Sammlung von Mikroorganismen und Zellkulturen GmbH).
2. Culture Medium:
    Complete RPMI: RPMI-1640 medium with 25 mM HEPES (4-(2-hydroxyethyl)-1-piperazineethanesulfonic acid) and L-glutamine (Gibco/Invitrogen™, Cat. #22400-089)+10% heat-inactivated fetal bovine serum (FBS) (Gibco/Invitrogen™, Cat. #16140-071)+1× Penicillin/Streptomycin (Gibco/Invitrogen, Cat. #15070-063)+50 ug/ml Plasmocin (Invivogen™, Cat. #ant-mpt)
    Phenol red free cRPMI: Phenol red free RPMI-1640 medium L-glutamine (Gibco/Invitrogen™, Cat. #Gibco/Invitrogen, 11835-030)+10% heat-inactivated fetal bovine serum (FBS) (Gibco/Invitrogen, Cat. #16140-071)+1× Penicillin/Streptomycin (Gibco/Invitrogen™, Cat. #15070-063)
3. Other Liquid Reagents:
    Promega™ MTS reagent (Cell Titer 96 Aqueous Cat. #G358B)
    Dimethyl sulfoxide (DMSO) (Sigma™, Cat. #D2650)
4. Consumable Supplies:
    Sterile 96-well polystyrene tissue culture-treated clear plates with lid (Falcon™, Cat. #3072)
5. Equipment:
    Platereader, 96-well (SpectraMAX GeminiEM™, Molecular Devices, USA)

B. Method

Day 1: Preparation of Test Compounds

Dissolve and serial-dilute test compounds in DMSO at 1000× concentration.

Dilute 1: 100 test compounds in phenol red free cRPMI in sterile 96-well polystyrene tissue culture plates Use a 12-channel pipetor to transfer 10 ul of diluted compound solution to the an empty 96 well plate to be used for cell incubation Following addition of 100 ul of cell cultures, the final concentration of test compounds would be 1×.

Day 1: Preparation of Liquid Tumor Cells for Compound Treatment

Harvest cells in complete RPMI from log-phase cultures at densities of approximately 0.3-0.7 million/ml. Count cells and adjust to 0.1 million/ml in phenol red free cRPMI (For fast growing cells with doubling time of equal or less than 24 hours, e.g. K562, use 0.05 million/ml instead to avoid overgrowing).

Transfer triplicates of 100 µl of cells to the wells of 96-well clear plates for a total of 10000 cells/well. Note that each well already contains 10 µl of 10× concentrated test compound prepared as above.

Cell Incubation

Incubate cells for 72-96 hours at 37° C. in a tissue culture incubator containing 5% $CO_2$.

C—Measurement: Determination of Cell Viability

1. Thaw the Promega's MTS reagent and add 20 ul to each well with a repeat pipetor.

2. Mix the reagent in the well by rocking the plate and place the plate to a CO2 tissue culture incubator at 370 C.

3. Prepare the "no cell" blank control by adding the MTS reagent to a row of wells containing 100 ul of phenol red free cRPMI alone.

4. Incubate at 370 C until the absorbance at 490 nm for the control cells is >1.5.

5. Mix the cell culture by rocking to ensure the color is uniform in the wells, making sure there are no air bubbles. If present, centrifuge the plate at 1000×g on a bench top centrifuge to eliminate air bubbles.

6. Read the absorbance in the Molecular Devices 96-well plate reader.

D-Analysis of Results:

1. Copy and paste the text data onto an Excel spreadsheet

2. Average the "no cell" blank data and subtract this value from the absorbance from each well containing cells.

3. Average the blank-corrected triplicate well data and compute standard deviation for replicate variation.

4. Average of control cell data:

5. Calculate the averaged compound-treated cell data as a percent of the averaged control cell data as follows:

(Compound-treated value/control value)*100=% of control value

Results:

We have determined the anti-proliferation activity of the compound of Formula I. As shown in Table 4, the compound of Formula I is consistently active in the two MCL cell lines of Jeko-1 and Granta-519. Furthermore, the compound of Formula I appears to be inhibitory against a relatively wide spectrum of hematological malignant cell lines (6 out of 15).

TABLE 4

Effects of Syk compound on viability of liquid tumor cell lines (MTS assay)

| Disease | Cell line | IC50 (uM) A003397769 N = 4 | % Inhibition at max. conc. (10 uM) A003397769 N = 4 |
|---|---|---|---|
| AML | HL-60 | 3.7, 8.1, >10, >10 | 35 |
| AML | KG-1 | 1.9 | 91 |
| AML | ML-2 | >10 | 28 |
| B-ALL | Nalm-6 | 5.5 | 84 |
| B-CLL | JVM-2 | 3.5, 3.6, 7.7, >10 | 60 |
| B-CLL | JVM-2 | 6.8, 7.0, 8.4, >10 | 59 |
| B-NHL | DLCL-2 | 1.4, >10, >10, >10 | 0 |
| B-NHL | DOHH-2 | 4.5 | 75 |
| CML | Jurl-MK1 | 1.2, >10, >10, >10 | 28 |
| CML | K562 | 3.9, >10, >10, >10 | 21 |
| MCL | Jeko-1 | 3.1 | 97 |
| MCL | Granta-519 | 3.4 | 67 |
| MM | L-363 | 5.5 | 61 |
| MM | RPMI8226 | >10 | 36 |
| T-ALL | Jurkat | 6.8, >10, >10, >10 | 43 |

Inhibition of Rat Collagen Induced Arthritis

Introduction

Collagen-induced arthritis (CIA) is a well characterized model of human rheumatoid arthritis (RA) that can be induced in genetically susceptible rodents following immunization with type II collagen (cII) in adjuvant. Both CIA and RA exhibit severe swelling/inflammation of the joints, synovial hyperplasia and cartilage and bone erosion. This chronic inflammatory arthritis induced by immunization with cII consists of both a T cell component, as evidenced by attenuated CIA in T cell-deficient mice and a B cell component. B cell-deficient mice, xid mice or mice with a null mutation in CXCR5 fail to develop CIA.

Methods:

Immunization and Challenge: Female Lewis rats were immunized on day 0 and challenged on day 7 with cII from bovine nasal mixed with Freund's incomplete adjuvant at a final collagen concentration of 1.0 mg/ml. The animals were injected at the base of the tail with 400 µg of cII.

Prophylactic Dosing Regimen: The compound of Formula I (3.0, 10, and 30 mg/kg) was orally dosed (p.o.) twice daily (b.i.d.) starting on day 6 and continued through day 21.

Combination Dosing Regimen: Rats were dosed with the compound of Formula I (3.0 and 10 mg/kg, p.o., bi.d.) or Methotrexate (MTX, 0.1 and 0.2 mg/kg, p.o., q.d.) as monotherapy or in combinations consisting of each dose of the compound of Formula I with each dose of MTX starting on day 6 and continuing through day 21.

Therapeutic Dosing Regimen: The compound of Formula I (10 and 30 mg/kg, p.o., b.i.d.) was orally administered starting on day 12 and continued through day 21.

Joint Pathology Ankle joint swelling was measured to the nearest 0.01 mm by using electronic digital calipers. Measurements were recorded 7 times throughout the study starting on day 6 and ending on day 21. Body weights were recorded on the same days. On day 21, hind paws were removed at the hairline just above the ankle and fixed in 10% neutral buffered formalin.

MicroCT analysis: Ankle joints were examined using a cone-beam µCT scanner. A scout view scan was obtained first for selection of the examination volume of the specimens, followed by positioning, measurement and computational reconstruction. In ankle joints, the ratio of bone surface to bone volume, describing the complexity of bone surface in a certain volume, was analyzed.

Statistical Analysis For joint swelling/inflammation, data were analyzed using Everstat v.5 software and a 2-way repeated measure ANOVA with Dunnett's post test. MicroCT data were analyzed by Everstat using a 1-way ANOVA and Newman-Keuls multiple comparison test. Data are presented as the mean±SEM and p values of <0.05 are considered significant.

Figure 2:
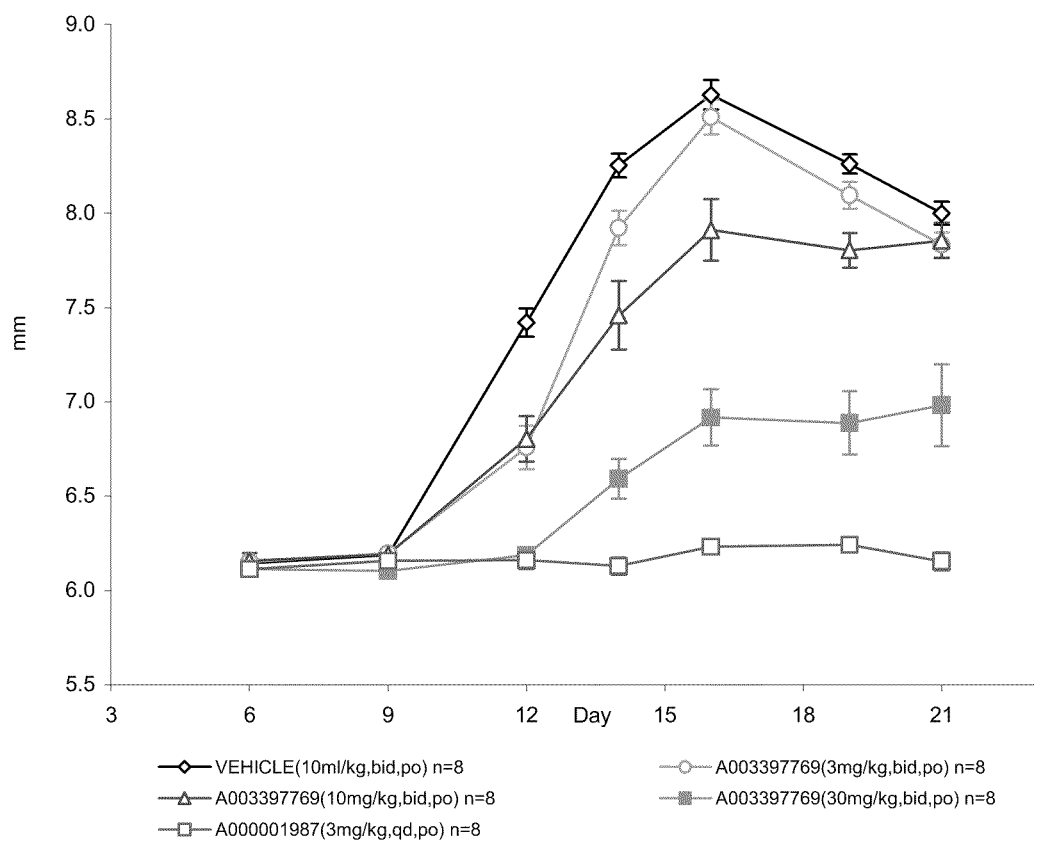
FIG. 2: Mean ankle joint diameter of rats injected with collagen type II from bovine nasal in Freund's incomplete adjuvant and treated with A003397769, the compound of Formula I (3.0, 10, or 30 mg/kg b.i.d.) from day 6 through day 21. Mean ankle joint diameters of female LEW rats sensitized by intra-dermal injection of collagen in Freund's incomplete adjuvant (400 ug/400 ul/rat) on Days 0 and 7. Animals dosed from Day 6-21.

Results:

Prophylactic Dosing:

Digital Caliper Measurements of Joint Swelling/Inflammation (FIG. 2).

The compound of Formula I (3.0 mg/kg) significantly reduced ankle swelling/inflammation compared to vehicle treated rats on day 12 only.

The compound of Formula I (10 mg/kg) significantly reduced ankle swelling/inflammation compared to vehicle treated rats on days 12 through 19.

The compound of Formula I (30 mg/kg) significantly reduced ankle swelling/inflammation compared to vehicle treated rats from day 12 through day 21.

Figure 3:
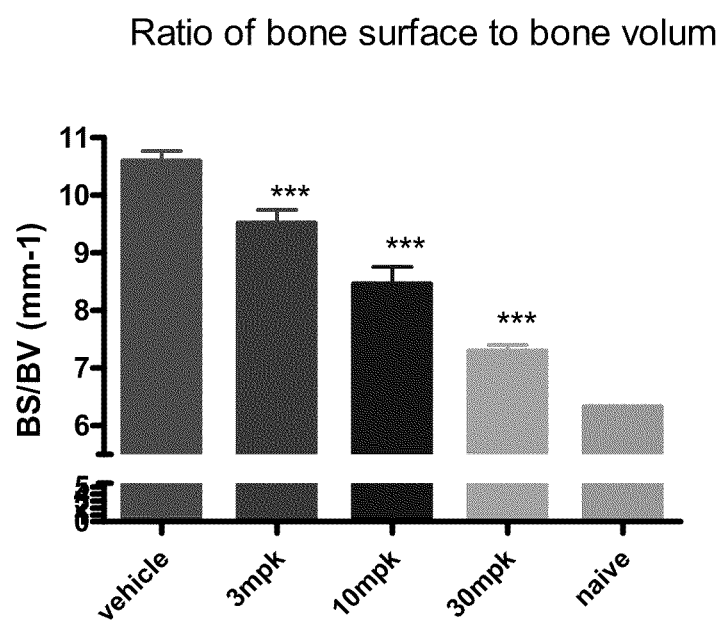
FIG. 3: Analysis of bone erosion (ratio of bone surface to bone volume) in the calcaneus of CIA rats treated with A003397769 (3.0, 10 or 30 mg/kg).

MicroCT Analysis (FIG. 3).

The compound of Formula I (3, 10 or 30 mg/kg, b.i.d.) demonstrated significant reductions in bone erosion when compared to the vehicle-treated rats (measured by the ratio of bone surface to bone volume).

Figure 4:
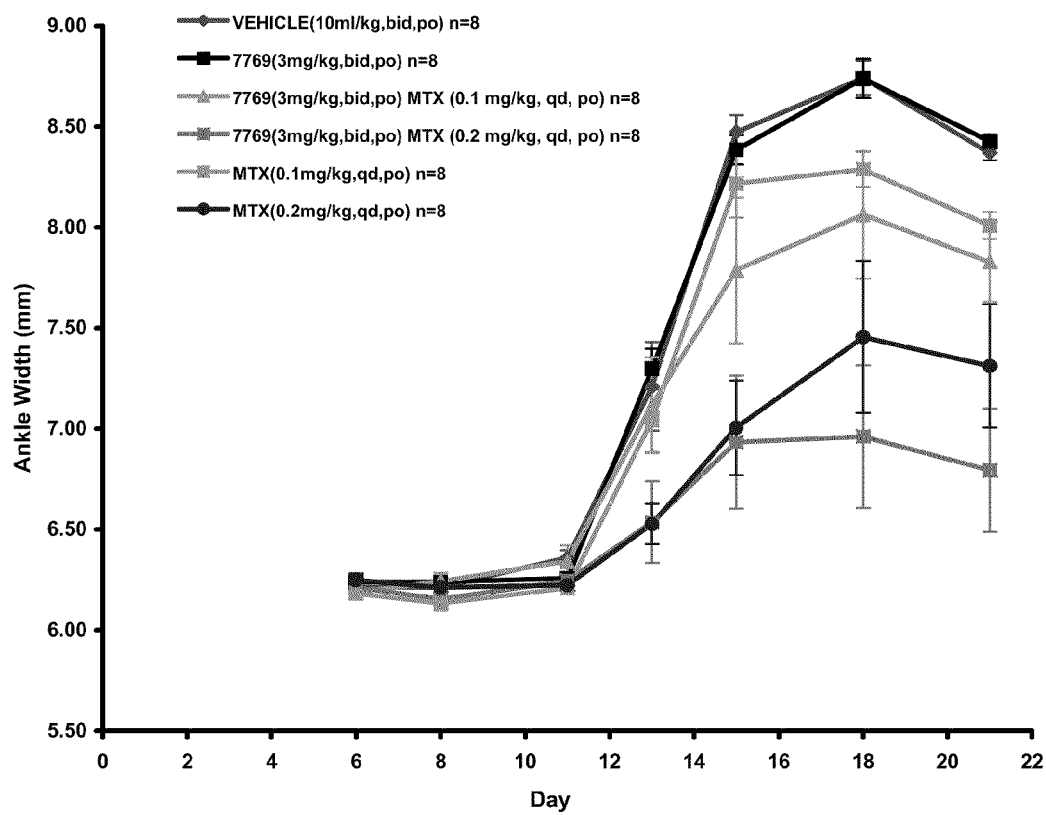
FIG. 4: Mean ankle joint diameter of rats injected with collagen type II from bovine nasal in Freund's incomplete adjuvant and treated with A003397769 (3.0 mg/kg) alone or in combination with Methotrexate (0.1 or 0.2 mg/kg) from day 6 through day 20 or 21 and compared to vehicle dosed animals. Effects of SYK Inhibitor, A003397769 (3.0 mg/kg b.i.d.), as Monotherapy or in Combination with Methotrexate on Rat CIA.
Figure 5:
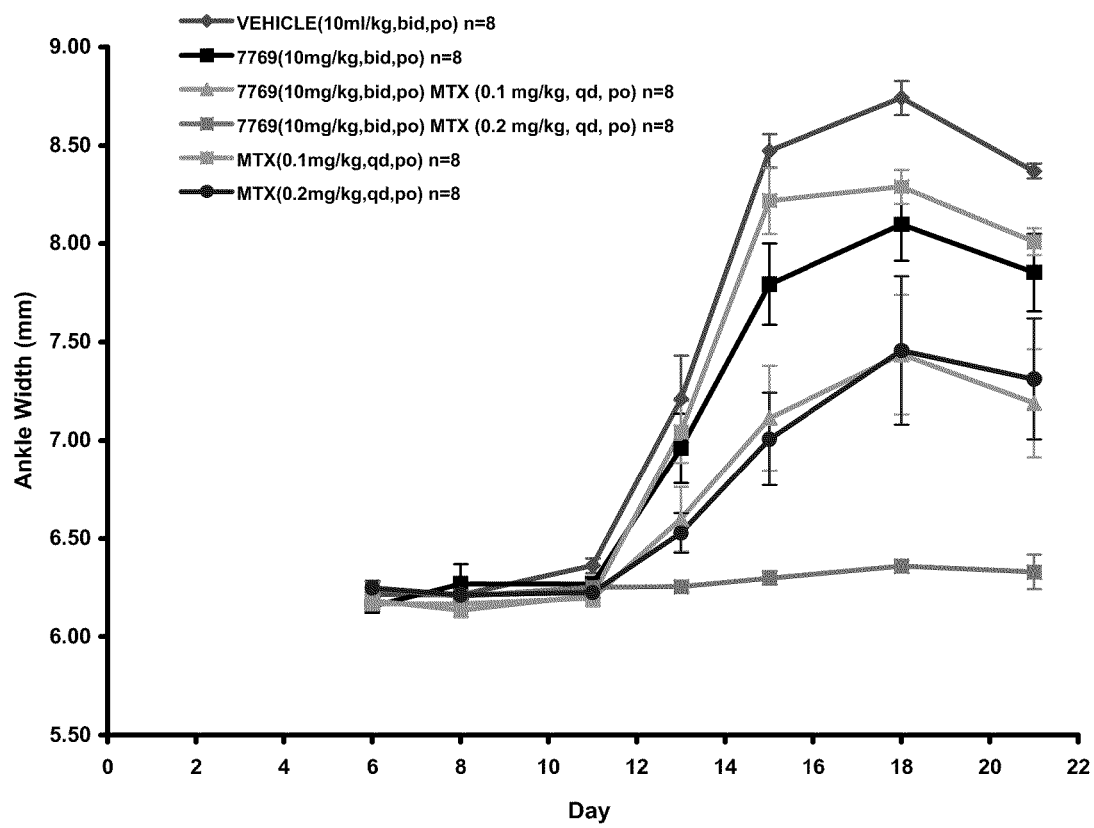
FIG. 5: Mean ankle joint diameter of rats injected with collagen type II from bovine nasal in Freund's incomplete adjuvant and treated with A003397769 (10 mg/kg) alone or in combination with Methotrexate (0.1 or 0.2 mg/kg) from day 6 through day 20 or 21 and compared to vehicle dosed animals. Effects of SYK Inhibitor, A003397769 (10 mg/kg b.i.d.), as Monotherapy or in Combination with Methotrexate on Rat CIA.

Combination Dosing:

Digital Caliper Measurements of Joint Swelling/Inflammation (FIG. 4, 5).

The compound of Formula I (10 mg/kg) significantly reduced ankle swelling/inflammation compared to vehicle-treated rats from days 15 through 21.

Combination therapy of the compound of Formula I (10 mg/kg) plus MTX (either 0.2 or 0.1 mg/kg) demonstrated a significant reduction in ankle swelling/inflammation from day 15-day 21 compared to that observed in rats dosed with either the compound of Formula I (10 mg/kg) or MTX (0.2 or 0.1 mg/kg) as monotherapy.

The compound of Formula I (3.0 mg/kg) as monotherapy or as combination therapy with MTX (0.1 mg/kg) failed to significantly impact on disease severity as measured by joint swelling/inflammation.

The compound of Formula I (3.0 mg/kg) as combination therapy with MTX (0.2 mg/kg) demonstrated a significant reduction in joint swelling/inflammation above what was observed when either drug was dosed as monotherapy on measurement taken from days 18 through 21.

Figure 6:
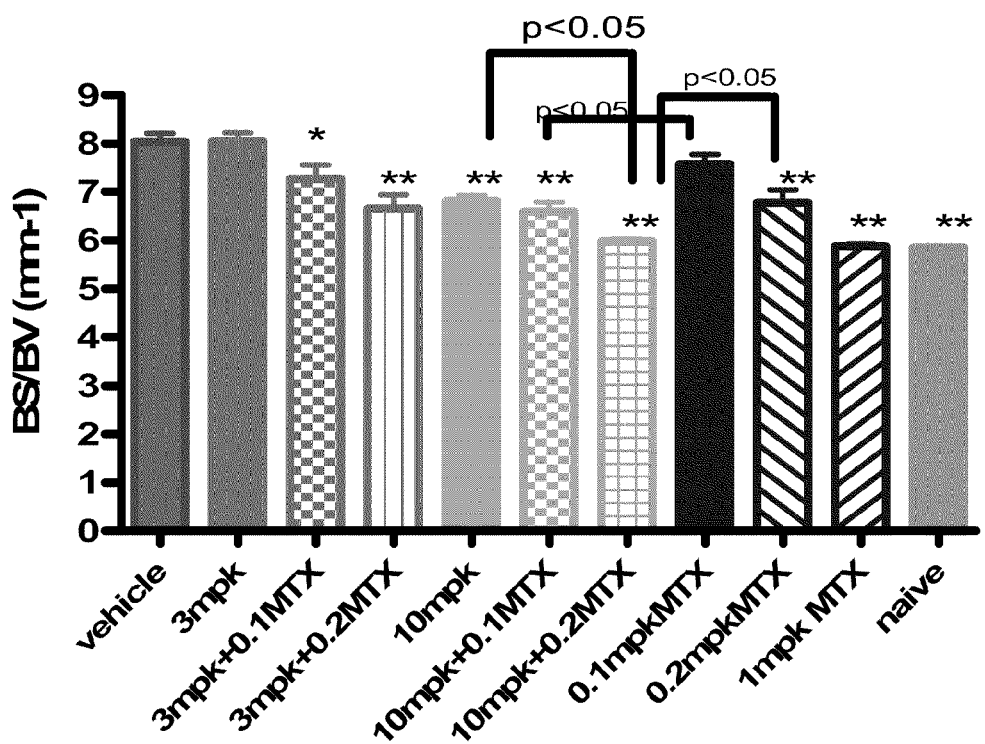
FIG. 6: Analysis of bone erosion (ratio of bone surface to bone volume) in the calcaneus of CIA rats treated with A003397769 (3.0 or 10 mg/kg) alone or in combination with Methotrexate (0.1 or 0.2 mg/kg).

MicroCT Analysis (FIG. 6):

Three-dimensional images demonstrated significant bone erosion/destruction in joints of vehicle-treated rats.

Dosing of rats with the compound of Formula I (10 mg/kg, po, bid) resulted in a significant decrease in bone erosion versus vehicle-treated rats. A significant decrease was not observed in rats dosed with 3 mg/kg the compound of Formula I.

Monotherapy with MTX (0.2 mg/kg, po, qd) resulted in a significant decrease in bone erosion. This effect was not seen in rats dosed with 0.1 mg/kg MTX.

When treated with combinations of the compound of Formula I and MTX, all groups showed a significant decrease in the ratio of bone surface to bone volume compared to vehicle-treated rats.

Combination therapy of the compound of Formula I (10 mg/kg, bid, po) with MTX (0.2 mg/kg, qd) resulted in additive protection from bone erosion versus that observed in rats receiving monotherapy with either the compound of Formula I or MTX.

Therapeutic Dosing

Figure 7:
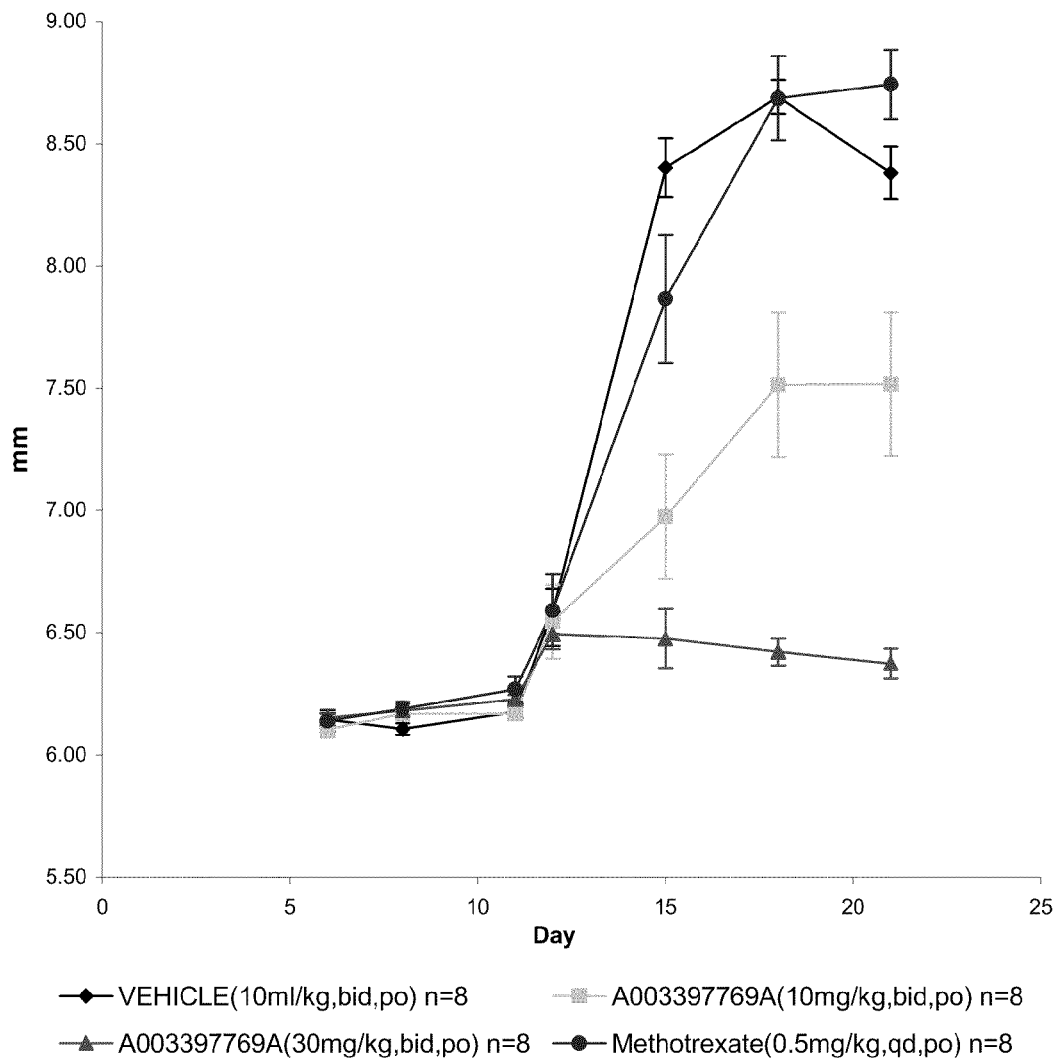
FIG. 7: Mean ankle joint diameter of rats injected with collagen type II from bovine nasal in Freund's incomplete adjuvant and treated therapeutically with A003397769A (10 and 30 mg/kg b.i.d) from day 12 through day 21. Mean Ankle Joint Diameters of Female Lewis Rats Sensitized by Intradermal Injection of Collagen in Freund's Incomplete Adjuvant (400 ug/400 ul/rat) on Days 0 and 7. Average of Both Paws.

Digital Caliper Measurements of Joint Swelling/Inflammation (FIG. 7).

Even when administered in a therapeutic regimen in which dosing was delayed until arthritis was visually evident, the compound of Formula I (10 and 30 mg/kg, p.o., b.i.d.) significantly reduced ankle swelling/inflammation from day 15-21

Figure 8:
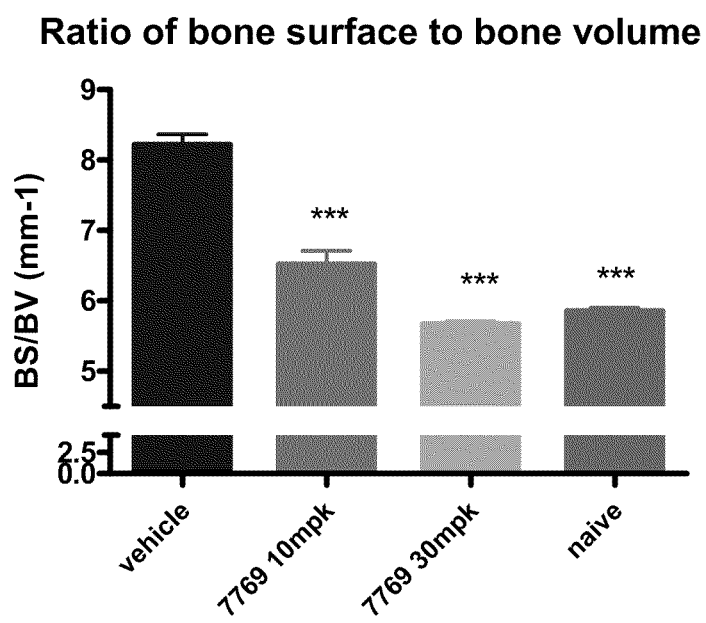
FIG. 8: Analysis of bone erosion (ratio of bone surface to bone volume) in the calcaneus of CIA rats treated therapeutically with A003397769A (10 or 30 mg/kg b.i.d.).

MicroCT Analysis (FIG. 8):

Compared to vehicle-treated, CIA rats dosed therapeutically with the compound of Formula I (10 mg/kg or 30 mg/kg) exhibited a significant decrease in bone erosion as measured by the ratio of bone surface to bone volume.

Summary:

These studies confirm that inhibition of syk kinase by the compound of Formula I can significantly delayed both the onset and progression of rat CIA as measured by decreased in joint swelling/inflammation and bone erosion. Importantly, significant inhibition of disease progression and severity were observed in rats in which dosing was delayed until visible signs of arthritis were evident. New clinical therapies for RA are normally given in combination with MTX. Our data in a rodent model of arthritis demonstrate additive effects when the compound of Formula I is dosed in combination with MTX indicating that combination therapy of the compound of Formula I and MTX could produce synergistic clinical effects in RA patients.

Angiogenesis Assay

Female Lewis rats (5 week-old, 150-175 g) were anesthetized using xylazine (4 mg/kg) and ketamine (80 mg/kg). Cellulose sponges (diameter 10 mm, Vivoxid Ltd.™, Turku, Finland) containing 50 µl of either FGF-2 (fibroblast growth factor 2) solution (containing 400 ng of FGF-2) or vehicle (physiological salt solution, bovine serum albumin 0.08%) were then implanted subcutaneously on the back of the animals. During the two following days further angiogenesis was induced by daily injection through the skin and into the sponges of 50 µl of FGF-2 solution or vehicle (basal conditions). One week after sponge implantation, animals were euthanized using an overdose of pentobarbital and the sponges were dissected out. The sponges were then minced and homogenized in lysis buffer (NaCl 150 mM, EDTA 1 mM, Triton X100 1%, sodium deoxycholate 0.5%, NaF 10 mM, Tris/HCl 30 mM pH 7.8 containing a protease inhibitor cocktail (P8340, Sigma-Aldrich™, St Louis, USA)) using Lysing Matrix D tubes (MP Biomedicals™, Illkirch, France) in a Fastprep homogenizer (Qbiogene™, Illkirch, France). Hemoglobin concentration, indicative of vascular volume, was determined using the Drabkin assay (Pierce Biotechnology™, Rockford, Ill., USA). Compounds were administered by oral gavage as a suspension in aqueous methylcellulose 0.6%, Tween 80 0.5% solution.

Figure 9:
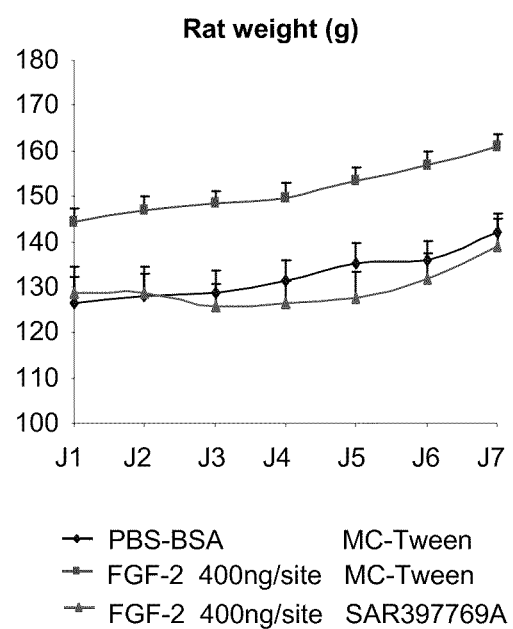
FIG. 9: Effect of the compound of Formula I on rat weight.
Figure 10:
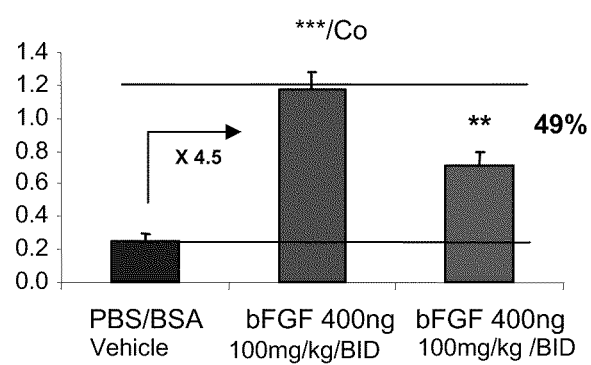
FIG. 10: Effects of the compound of Formula I on hemoglobin concentration.

The effects of the compound of Formula I on rat weight are shown in FIG. 9. The effects of the compound of Formula I on hemoglobin concentration (mg/ml) are shown in FIG. 10.

What is claimed is:

1. A compound of formula (I):

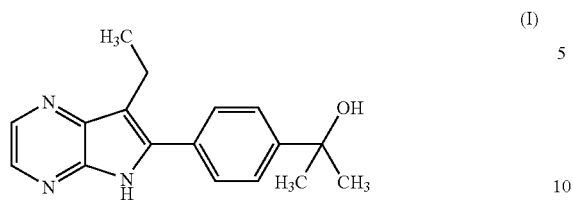

or a corresponding N-oxide, or a prodrug; or a pharmaceutically acceptable salt of such of compound; or an N-oxide or a prodrug of the salt.

2. A pharmaceutical composition, comprising a compound according to claim 1, together with at least one pharmaceutically acceptable carrier or excipient.

3. The compound according to claim 1, wherein the salt is selected from:

hydrochloride, hydrobromide, sulphate, phosphate, nitrate, sulfamate, acetate, citrate, lactate, tartrate, malonate, oxalate, salicylate, propionate, succinate, fumarate, maleate, methylene-bis-b-hydroxynaphthoate, gentisate, isethionate, di-p-toluoyltartrate, methane-sulfonate, ethanesulfonate, benzenesulfonate, p-toluenesulfonate, cyclohexylsulfamate and quinate.

4. The compound according to claim 1, wherein the salt is hydrochloride.

5. The compound according to claim 1, wherein the salt is acetate.

6. The compound according to claim 1, wherein the salt is citrate.

* * * * *

UNITED STATES PATENT AND TRADEMARK OFFICE
CERTIFICATE OF CORRECTION

PATENT NO. : 8,658,649 B2
APPLICATION NO. : 12/401254
DATED : February 25, 2014
INVENTOR(S) : Timothy A. Gillespy et al.

It is certified that error appears in the above-identified patent and that said Letters Patent is hereby corrected as shown below:

On the Title Page:

Under "Other Publications" on page 1, right-hand column, item (56), line 8, please replace "1998" with --1996--.

In the Claims:

At column 19, claim number 1, line number 13, please replace "of such of" with --of such--.

Signed and Sealed this
Twenty-ninth Day of March, 2016

Michelle K. Lee
*Director of the United States Patent and Trademark Office*